United States Patent [19]

Martin

[11] 4,279,252

[45] Jul. 21, 1981

[54] X-RAY SCALING CATHETER

[76] Inventor: Michael T. Martin, 607 N. Chippewa Apt. #151, Anaheim, Calif. 92801

[21] Appl. No.: 69,312

[22] Filed: Aug. 24, 1979

[51] Int. Cl.³ .............................................. A61M 25/00
[52] U.S. Cl. ................................ 128/349 R; 250/491; 128/658
[58] Field of Search .............................. 128/656–658, 128/695, DIG. 9, 349 R; 33/174 D, 125 R, 137 R; 250/491

[56] References Cited

U.S. PATENT DOCUMENTS

| | | | |
|---|---|---|---|
| 3,847,157 | 11/1974 | Caillovette | 128/656 |
| 4,048,507 | 9/1977 | Gaston | 250/491 |
| 4,111,190 | 9/1978 | Plumridge | 128/658 |

*Primary Examiner*—Hiram Bernstein
*Attorney, Agent, or Firm*—George W. Finch

[57] ABSTRACT

A standard angiography catheter is modified by placing at least two radio opaque markers therein a known distance apart adjacent its distal end to enable the calculation and correction of errors due to X-ray magnification.

8 Claims, 1 Drawing Figure

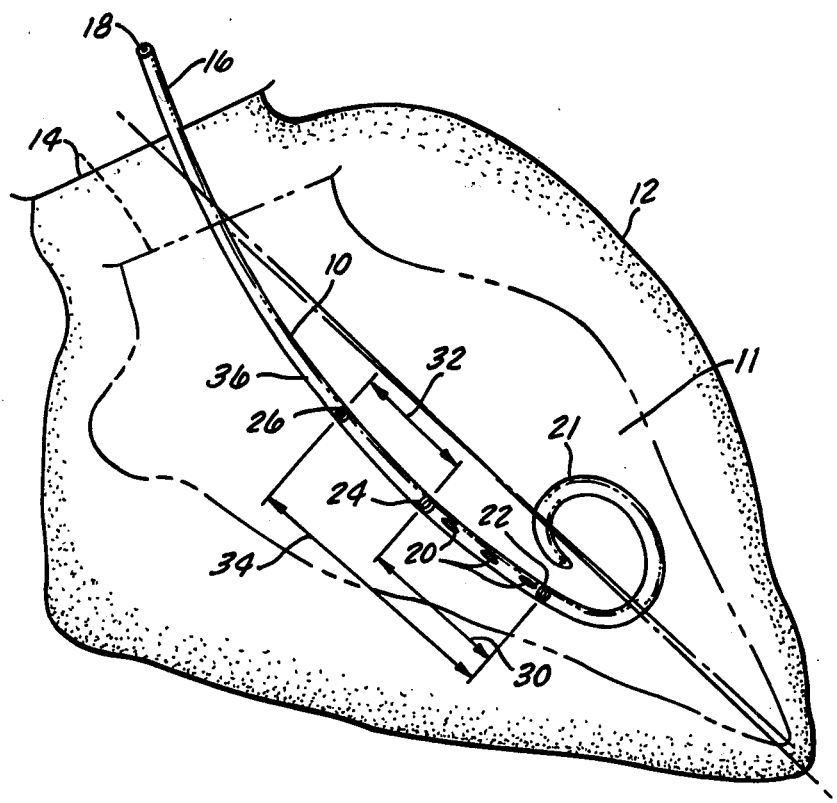

X-RAY SCALING CATHETER

BACKGROUND OF THE INVENTION

Normal radiography is performed using essentially a point source of X-rays whose beams expand, pass through the tissue being investigated and expose an X-ray sensitive emulsion in accordance with the attenuated intensity of the X-rays. Since the X-rays are not projected in parallel beams, exact size determinations of the tissue are difficult from observation of the exposed emulsion. This is because the angled beams cause magnification which is dependent upon the distances between the point source, the portions of the patient of interest, and the emulsion.

Devices such as the devices shown in U.S. Pat. No. 4,048,507 can be used to determine the magnification at predetermined locations between an X-ray source and the emulsion film. However, for these determinations to provide accurate results in certain diagnostic procedures, the exact relative location of the organ being investigated also must be known. Since patients' physiologies vary greatly, especially when disease or abnormalities are involved, there has been a need to provide a scaling device which can be located centrally within the organ of interest so that the magnification factor can be determined.

The inability to determine magnification is a particularly acute problem in angiographic estimation of left ventricular volume of a patient's heart. Most methods assume the left ventricular chamber to be ellipsoidal in shape and the following is a typical emperical equation for determining the volume:

$$\text{Volume}_{true} = 0.18 \left( \frac{8}{3\pi} \times \frac{A^2}{L} \right) + 1.9 \text{ ml} \qquad \text{Equation (1)}$$

where A=planimetered area of ventricular cavity silhouette, and L=the longest length of ventricular cavity silhouette.

The small standard errors observed in volume estimates derived from angiograms indicate that the geometry, orientation, and shape of the left ventricular cavity in the thorax are mathematically predictable with a high degree of accuracy. Conversely, the extent to which the estimates of volume may be effected by changing the orientation of the left ventricular cavity in relation to the radiographic filming plane shows that the accuracy of any angiographic estimate of volume depends on a normal orientation of the left ventricular cavity in the chest and the knowing of its location, particular when single plane films are used.

Magnification of the cavity silhouette results because the non-parallel X-ray beams originate from a virtual point source and because short filming distances are used in cardiac angiography. The degree of magnification can be determined by knowing the height of the left ventricular chamber from the X-ray tube focal spot ($h_1$), the distance from the focal spot to the film or in the case of cinefluoragraphy, the input phosphor of the image intensifier (h) and the measured image semi-axes ($a_1$). The true semi-axes (a) can be calculated using the parallax method or similar sides of similar triangles hypothesis as shown.

$$a = a_1 h / h_1 \qquad \text{Equation (2)}$$

The location of the level of the left ventricular cavity is difficult to determine while the patient is in the position of filming because the whole procedure is performed either with the X-ray source and X-ray detector at an angle to vertical or with the patient at an angle to vertical. Heretofore the common method has been to use a one centimeter square grid filmed after the patient has been filmed and placed at what is the estimated to be the level of the center of the patient's left ventricular cavity. The method has two advantages. First it allows the film to be projected for the purposes of measurement at any field size eliminating one potential source of error, and secondly the degree of image magnification can be determined from the ratio of the known or true area of a block of squares in the grid and the area of this block drawn from the projected film and measured with a compensating polar planimeter. However, to be useful the grid must be located at the right height and this is almost impossible to determine accurately especially if abnormal physiology is involved.

Some investigators have suggested the magnification correction factors can be derived from measurement of the diameter of the cardiac catheter used in the angiogram knowing its true external diameter. This has proved to be a source of large error in the calculation of the volume because the X-ray beam does not originate from a true point source but from a focal spot of finite width. X-rays from both sides of the focal spot demarcate the edges of the catheter so that the margin of the X-ray image exhibits a double edge or penumbera. The indistinct margin which results from the penumbera effect is particularly apparent in objects of smaller dimensions such as the catheter's width and can result in an error of approximately 50% in the volume estimation at conventional filming distances.

Therefore, there has been a need to provide means for calibrating the magnification factor of X-ray studies particularly during angiographic estimation of left ventricular volume which has been unsolved heretofore.

BRIEF DESCRIPTION OF THE PRESENT INVENTION

In the present invention a standard catheter having an angiography pigtail is modified so that it has two or more radio opaque markers a predetermined distance apart adjacent its distal end, proximal and distal to the side holes of the catheter. These radio opaque markers usually take the form of rings about the catheter so that when viewed on a X-ray film, they appear as lines if viewed perpendicular or ovals if viewed at other than a perpendicular orientation. The radio opaque markers are spaced a substantial distance such as 1.35 cm apart so that any error due to penumbera is greatly reduced. Also the edge of the radio opaque markers is more easily determined since it provides a more contrasty indication than the edge of the catheter.

When used to introduce radio opaque dye into the heart, the catheter is inserted into the left ventricular chamber where the motions of the heart tend to keep it centrally located. Therefore the radiographic study not only indicates the outline of the heart but at the same time provides a measuring scale which thereafter can be used without resort grids whose location must be estimated to provide accurate results.

It is therefore an object of the present invention to improve the angiographic estimation of left ventricular volume by providing a catheter having means thereon for estimating X-ray magnification.

Another object is provide an angiographic catheter having X-ray magnification determining means thereon which is easily constructed, does not needlessly in danger the patient and requires no estimation of heart location.

These and other objects and advantages of the present invention become apparent to those skilled in the art after considering the following detailed specification in which a preferred embodiment is described in conjunction with the accompanying drawing.

BRIEF DESCRIPTION OF THE DRAWING

The drawing shows the silhouettes of the left ventricular cavity of a heart in its systolic and diastolic condition having a catheter positioned therein constructed according to present invention.

DETAILED DESCRIPTION OF THE SHOWN EMBODIMENT

Referring to the drawing more particular by reference numbers, number 10 refers to a angiographic catheter constructed according to the present invention. The catheter 10 is shown inserted in the left ventricular chamber 11 of a human heart 12 whose diastolic condition is shown in solid outline and whose systolic condition is shown in dashed outline. The catheter 10 is inserted through the aortic valve 14 for introducing radio-opaque dye in the left ventricular chamber 11 for performing angiographic estimation of the left ventricular volume. Views as shown in the FIGURE can only be obtained through radiographic techniques at the present time. The catheter 10 is formed by a hollow tube 16 having a passageway 18 therealong through which the radio-opaque dye can be forced. The dye exits the catheter 10 through a plurality of sidewardly facing holes 20 so that the interior of the left ventricular chamber 11 can be illuminated and determined on the X-ray film. A curved distal end or "pigtail" 21 is provided beyond the holes 20 to enable the catheter 10 to be guided as desired within the heart 12.

As aforesaid, to measure the volume of the left ventricular chamber 11, the magnification due to the essentially point source X-ray and flat plate film must be determined. Therefore the catheter 10 includes a plurality of radio opaque rings 22, 24 and 26 adjacent the distal end 21 thereof. It is preferable that the rings 22 and 24 are on the distal and proximal sides of the holes 20 since it is desirable that the dye being expelled from the holes 20 is expelled centrally within the chamber 11 and it is that location that gives the most accurate correction factor results.

It also is preferable that the catheter 10 and the chamber 11 in which it is resident is perpendicular to the X-ray beam during the procedure. When this is not the case as shown in the FIGURE, the rings 22, 24 and 26 appear to be ellipses rather than straight lines across the catheter 10 enabling the operator to reposition the patient or calculate the amount of foreshortening of the distance 30 or 32 or 34 between the rings 22, 24, or 26 so that the magnification factor on the exposed film can be determined to provide a correction factor for the volume calculation.

The rings 22, 24 and 26 can be constructed easily by embedding relatively radio opaque material such as aluminum foil within the plastic material forming the wall 36 of the catheter 10. Although as shown in scale, the rings 22, 24 and 26 are 1.35 cm apart, other suitable distances can be considered dependent upon the expected size of the left ventricular chamber 11. For example, such a procedure performed on infants would require closer spacing of the rings 22, 24 and 26, whereas large animal studies might require a larger spacing.

Thus there has been shown and described means to determine the X-ray magnification during angiographic estimation of left ventricular volume which fulfills all the objects and advantages sought therefore. Many changes, modifications, variations, and other uses and applications of the subject invention will become apparent to those skilled in the art however after considering this specification together with the accompanying drawing. All such changes, modifications, variations and other uses and applications which do not depart from the spirit and scope of the invention are deemed to be covered by the invention which is limited only by the claims which follow.

What is claimed is:

1. A catheter adapted for determining the magnification factor of an image produced by radiography including:
    a tubular portion sized and adapted for insertion through a blood conduit in a living body; and
    at least two indicia positioned along said tubular portion a predetermined distance apart, said indicia being constructed from material which is relatively radio-opaque with respect to the material from which said tubular portion is constructed so said at least two indicia can be observed in the image no matter what the relative radial orientation of said tubular portion and said at least two indicia with respect to the radiation of the radiographic procedure wherein said indicia are rings of radio-opaque material, when said tubular portion is in a linear orientation, said rings being parallel to each other.
2. The catheter as defined in claim 1 wherein said tubular portion includes:
    a sidewall; and
    a passageway bounded by said sidewall for conduction of radio-opaque dye into the blood of the body, said sidewall defining at least one sidewardly facing hole for the passage of the radio-opaque dye from said passageway to the blood of the body, said defined hole being located between at least two of said at least two indicia so that radio-opaque dye is dispensed into the blood therebetween.
3. The catheter as defined in claim 2 wherein said at least two indicia are formed from metal foil embedded in said sidewall.
4. The catheter as defined in claim 3 wherein said indicia are rings of metal foil, said rings having a predetermined width which is less than the width of the tubular portion and being orientated so that when said tubular portion between said rings is in a linear condition, said rings are parallel to each other and at right angles to said tubular portion.
5. An angiography catheter adapted for determining the magnification factor of a ventricular cavity image produced by radiography including:
    a hollow conduit portion adapted for extension through at least a portion of a blood conduit of a living body and placement in the ventricular cavity of the living body; and
    at least two separated markers positioned along said hollow conduit portion a predetermined distance apart, said markers being constructed from material which is relatively radio-opaque with respect to the material from which said hollow conduit portion is constructed so said markers appear in the ventricular cavity image no matter what the rotative position of said hollow conduit wherein said hollow conduit portion has a longitudinal axis, said markers each being rings of radio-opaque material which extend radially about a portion of said hollow conduit portion at right angles to said longitudinal axis.

6. The catheter as defined in claim 10 wherein said hollow conduit portion includes:
 a sidewall; and
 a passageway bounded by said sidewall for conduction of radio-opaque dye into the ventricular cavity of the body, said sidewall defining at least one sidewardly facing hole for the passage of the radio-opaque dye from said passageway to the body, said defined hole being located between at least two of said at least two markers.

7. The catheter as defined in claim 6 wherein said at least two markers are formed from metal foil embedded in said sidewall, each in the shape of a radial ring.

8. The catheter as defined in claim 7 wherein said ring shaped markers have a predetermined width along the length of said hollow conduit which is less than the width of said hollow conduit.

* * * * *